United States Patent [19]
Hanawa et al.

[11] Patent Number: 6,024,984
[45] Date of Patent: Feb. 15, 2000

[54] COMPOSITION CONTAINING AN EXTRACT FROM MUIRAPUAMA ROOT AND PLANT WORM EXTRACT

[75] Inventors: Masaaki Hanawa; Hideaki Kitajima; Kenji Tsunoda, all of Tokyo, Japan

[73] Assignee: Taisho Pharmaceutical Co., Ltd., Tokyo, Japan

[21] Appl. No.: 09/077,869

[22] PCT Filed: Dec. 20, 1996

[86] PCT No.: PCT/JP96/03733

§ 371 Date: Jun. 4, 1998

§ 102(e) Date: Jun. 4, 1998

[87] PCT Pub. No.: WO97/24134

PCT Pub. Date: Jul. 10, 1997

[30] Foreign Application Priority Data

Dec. 27, 1995 [JP] Japan ..................................... 7-340680

[51] Int. Cl.[7] .......................... A01N 63/00; A01N 65/00; A61K 35/12; A61K 35/64; C12N 5/00
[52] U.S. Cl. ........................ 424/520; 424/93.3; 424/93.7; 424/195.1; 424/538; 435/410
[58] Field of Search .................... 424/520, 93.1, 424/93.7, 538, 195.1, 93.3; 435/325, 348, 408, 410, 418; 514/885, 922

[56] References Cited

U.S. PATENT DOCUMENTS 5,702,691 12/1997 Ichinose et al. .................... 424/70.1

FOREIGN PATENT DOCUMENTS

94/02160 2/1994 WIPO .......................... A61K 35/78

OTHER PUBLICATIONS

Dialog Information Services, File 377, Derwent Drug File, Dialog Accession No. 00510368, Derwent accession No. 92–51335, Tadano T et al: "Pharmacological Studies of Nutritive and Tonic Crude Drugs on Fatigue in Mice. (Jap.)"; & Folia Pharmacol. Jpn. 100, No. 5, 423–31, 1992.

International Search Report.

Wu, "Tonic wine cont. bio. pro. of ant & silk moth" CN Abstr. 1996.

JP Abstr. Taisho Phaim Co. Ltd. "Hypersensit. drug useful . . . " JP Pat. 8048639/JP–94–79847, 1994.

Wu, "Oral liquid cont. biol. prod. of snail & turtle" CN 1126616, 95–101110, 1995. Abst. only.

*Primary Examiner*—David M. Naff
*Assistant Examiner*—Deborah K. Ware
*Attorney, Agent, or Firm*—Sughrue, Mion, Zinn Macpeak & Seas, PLLC

[57] ABSTRACT

A composition containing natural drugs is disclosed. The composition is effective for relieving physical and mental fatigue and for ameliorating a weakened constitution without any side effects, even if administered for a long time.

1 Claim, 2 Drawing Sheets

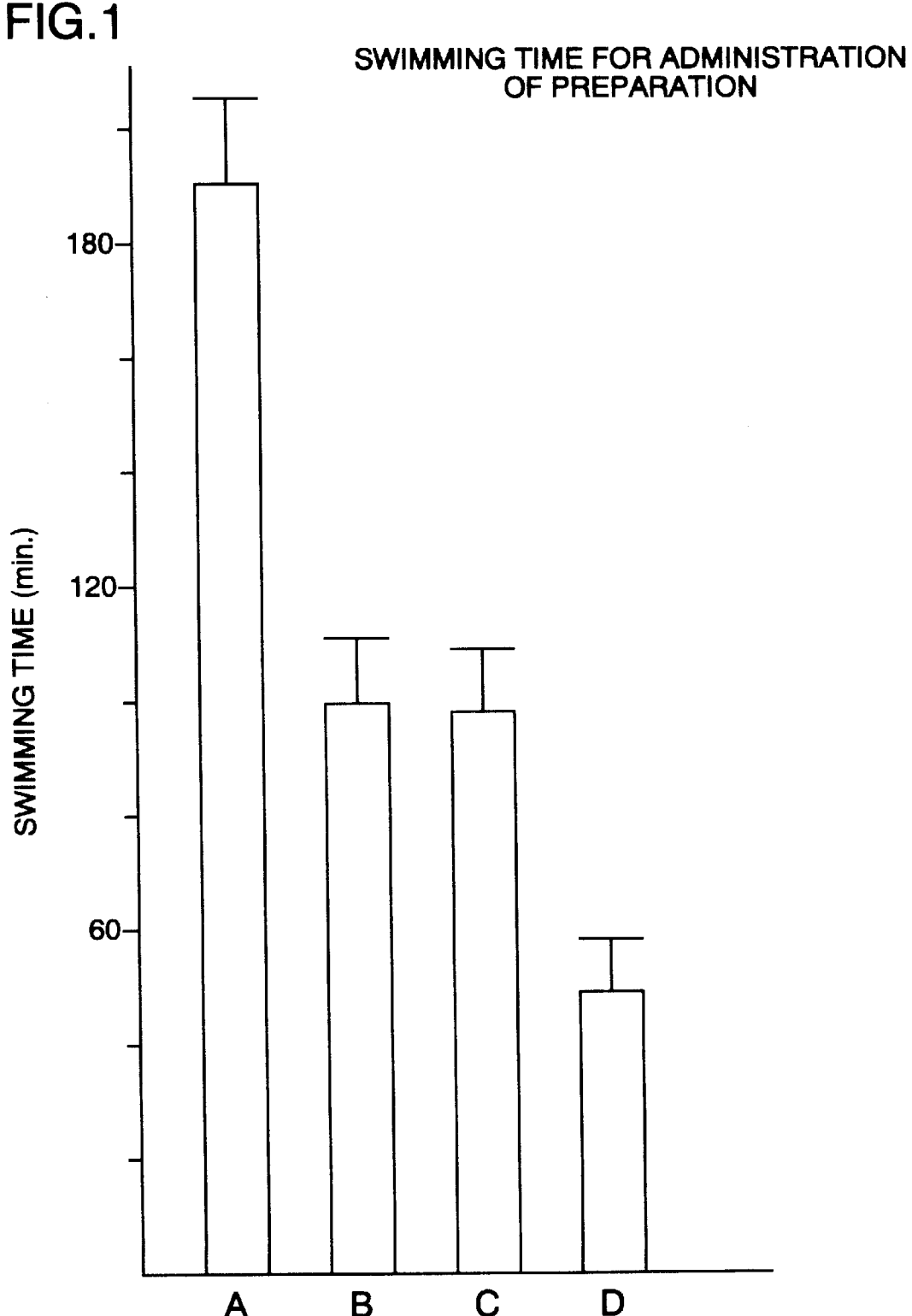

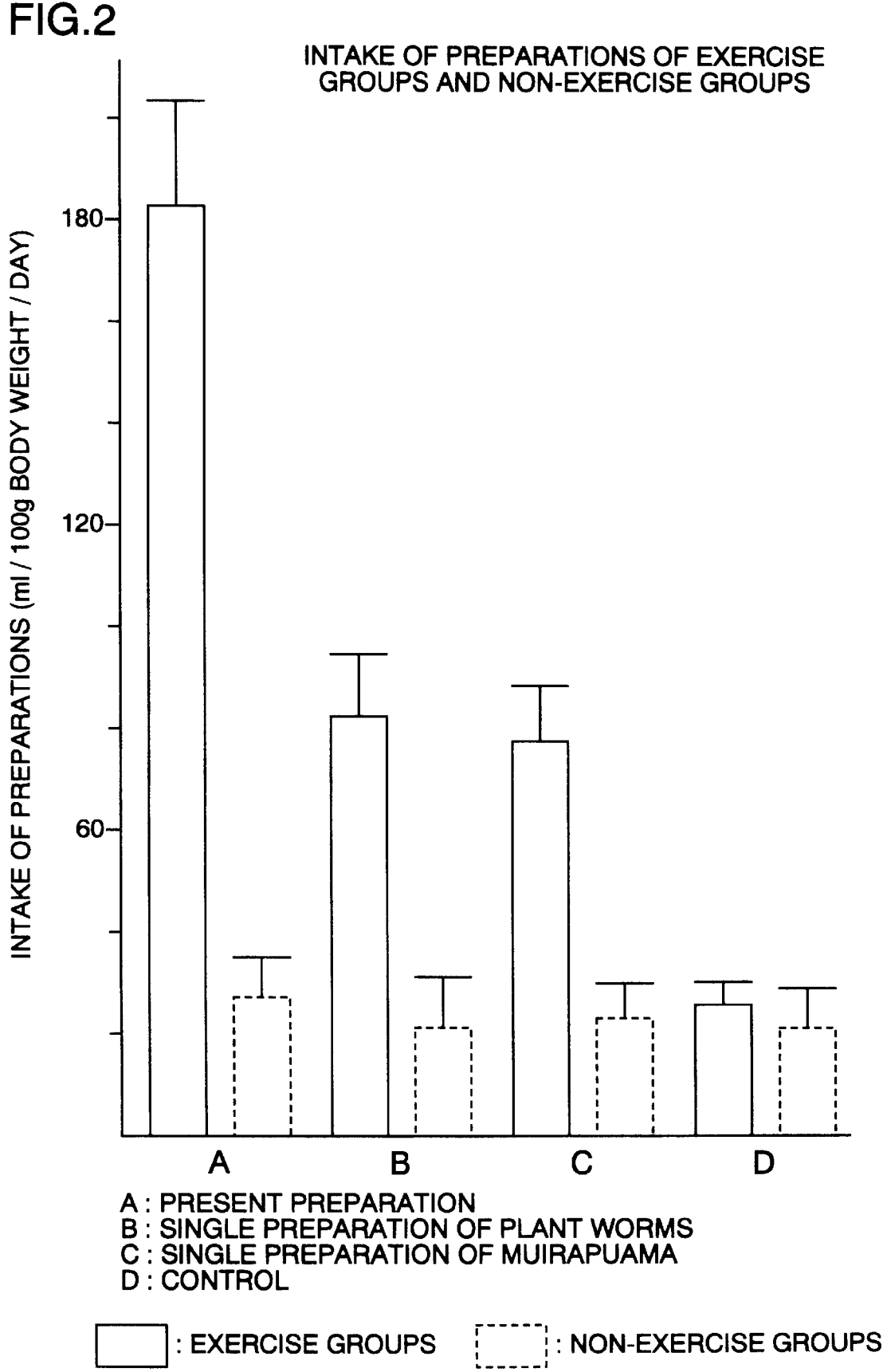

I, 024,984

COMPOSITION CONTAINING AN EXTRACT FROM MUIRAPUAMA ROOT AND PLANT WORM EXTRACT

BACKGROUND OF THE INVENTION

1. Field of the Invention

The present invention relates to a composition directed to relieving physical and mental fatigue and also to ameliorating or restoring a weakened constitution, etc., which comprises muirapuama and plant worms.

2. Description of the Related Art

Muirapuama is a natural drug used in the Amazon river basin in the old days as an invigorating or restoring tonic. Plant worms are also a natural drug used in China in the old days as a sedative or an antitussive.

Orally administering compositions containing a muirapuama extract or an extract of plant worms alone as an effective ingredient are known, but a composition containing both muirapuama and plant worms together is not yet disclosed.

Dialog Information Service, File 377, Derwent Drug File, Dialog Accession No. 00510368, Derwent Accession No. 92-51335 describes the use of a composition comprising muirapuama for the treatment of physical and mental fatigue.

An object of the present invention is to provide a composition having the intensified restoring effect of muirapuamna on depressed physical strength or stamina due to stress by combining with plant worms; having the effect of relieving stress and physical fatigue; and having the effect of ameliorating or restoring a weakened constitution without any side effects, even if administered for a long time.

SUMMARY OF THE INVENTION

As a result of extensive studies, the present inventors have found a novel combination of muirapuama with plant worms, which has a synergistic effect on relieving physical and mental fatigue due to stress, and ameliorating a weakened constitution, where muirapuama can effectively normalize stress, that is, disturbances in bodies due to various external and internal factors and plant worms can effectively promote metabolism and relieve physical and mental fatigue such as a general feeling of weariness, drowsiness, and a feeling of expansion.

According to the present invention, there is provided a composition comprising muirapuama and plant worms as effect ingredients for relieving physical and mental fatigue, stress, and ameliorating a weakened constitution or recovery therefrom, without any side effects, even if administered for a long time.

Original plants for muirapuama for use in the present invention are shrubs of family Olacaceae growing in the Amazon river basin in Brazil, including such species as *Ptychopetalum olacoides, Ptychopetlum uncinatum*, and *Liriosma ovata*, among which, the species *Ptychopetalum olacoides* is preferable. Needless to say, the species *Ptychopetlum uncinatum* and *Liriosma ovata* can also be used. In the present invention, roots of these original plants are used.

Plant worms are stomas of preferably the genus Cordyceps of family Clavicipitaceae and larvas of insects on which the genus Cordyceps are parasitic. Those of genuses Simizuomyces, Podonectrioides, and Torrbiella of the same family Clavicipitaceae can be also used.

The muirapuama of the present invention can be used as an extract and the extract can be obtained in the following manner:

Finely shredded muirapuama roots are mixed with dilute ethanol and subjected to infusion for 2 days with occasional stirring, and the resulting infusion is filtered. The residues are further mixed with dilute ethanol and subjected to infusion for 2 days with occasional stirring and the resulting infusion is also filtered. The resulting two filtrates are combined together and concentrated under reduced pressure to obtain a muirapuama extract.

The plant worms of the present invention can be used as an extract or a fluid extract and the extracts can be obtained in the following manner:

Rough-shredded plant worms are mixed with dilute ethanol and left standing at room temperature for about 2 hours, and then the resulting solution is further mixed with dilute ethanol and subjected to infusion by leaving the solution standing at room temperature for 3 days to obtain an extract as an infusion. The thus obtained extract is left standing at room temperature for 2 days and filtered through a filter paper to obtain a fluid extract.

According to the present invention, the effective dosage of muirapuama extract, for an adult is 10 to 5,000 mg/day, preferably 50 to 1,500 mg/day in terms of bulk natural drug, and the effective dosage of fluid extract of plant worms for an adult is 10 to 5,000 mg/day, preferably 50 to 1,000 mg/day in terms of bulk natural drug. That is, 0.002 to 500 parts by weight, preferably 0.03 to 30 parts by weight, more preferably 0.5 to 8 parts by weight, of a muirapuama extract is used per part by weight of a fluid extract of plant worms in terms of bulk natural drugs.

The present composition can contain caffeine; water-soluble vitamins, such as vitamin $B_1$, vitamin $B_2$, vitamin $B_6$, vitamin $B_{12}$, vitamin C, biotin, carnitine, pantotenic acid, and nicotinic acid and their derivatives; fat soluble vitamins, such as vitamin A, vitamin E and their derivatives; taurine; amino acids, such as arginine; and other natural drugs, such as extracts or tinctures of agkistrodon, ginseng, astragalus root, polygonati root, licorice, poria sclerotium, rehmannia root, Japanese angelica root, lycii fruit, cinnamon bark, velvet horm, barren-worts, cistanchis caulis, Chinese gutta percha, schisandra fruit, eleutherococc, ophiopogon tuber, polygoni multiflori root, and bovine bile.

The present composition can be administered or taken directly as is, or as medical preparations, for example, preparations for oral administration (e.g., granules, powder, capsules, tablets, dry syrup, liquid preparations) or injection, or foods, for example, soft drinks or solid foods (e.g., biscuits), prepared by mixing with other known additives, for example, a vehicle, a disintegrator, a binder, a lubricant, an antioxidant, a coating agent, a coloring agent, a corrigent, a surfactant, a plasticizer, a pH regulating agent, a refreshing agent, a suspending agent, a defoaming agent, a thickening agent, a dissolving aid, etc., according to ordinary methods or can be added to soft drinks or food as a functional ingredient or an additive.

According to the present invention, a single composition of a muirapuama extract and a single composition of an extract of plant worms can be sealed in separate ampules, respectively, and used upon mixing of the single composition or used without the simultaneously mixing when administered.

The vehicle includes, for example, a sugar alcohol such as D-mannitol, xylitol and D-sorbitol; saccharides such as glucose, sucrose, lactose and fruit sugar, crystalline cellulose, sodium carmellose, calcium hydrogen phosphate, wheat starch, rice starch, corn starch, potato starch, dextrin, β-cyclodextrin, light anhydrous silicic acid, titanium oxide, and magnesium metasilicate aluminate.

The disintegrator includes, for example, low-substituted hydroxypropyl cellulose, calcium carboxymethyl cellulose, sodium croscarmellose hydroxypropyl starch, and partially gelatinized starch.

The binder includes, for example, methyl cellulose, hydroxypropyl cellulose, hydroxypropylmethyl cellulose, polyvinylpyrrolidone, gelatin, gum arabic, ethyl cellulose, polyvinyl alcohol, pullulan, gelatinized starch, agar, tragacanth, sodium alginate, and propylene glycol alginate.

The lubricant includes, for example, stearic acid, magnesium stearate, calcium stearate, polyoxyl stearate, cetanol, talc, hydrogenated oil, sucrose fatty acid ester, dimethylpolysiloxane, yellow beeswax, and white beeswax.

The antioxidant includes, for example, dibutylhydroxytoluene (BHT), propyl gallate, butylhydroxyanisole (BHA), tocopherol, and citric acid.

The coating agent includes, for example, hydroxypropylmethyl cellulose, hydroxypropyl cellulose, methyl cellulose, ethyl cellulose, hydroxypropylmethyl cellulose phthalate, hydroxypropylmethyl cellulose acetate succinate, carboxymethylethyl cellulose, cellulose acetate phthalate, polyvinyl acetal diethylaminoacetate, aminoalkyl methacrylate copolymer, hydroxypropylmethyl cellulose acetate succinate, methacrylic acid copolymer, polyvinyl acetate diethylaminoacetate, and shellac.

The coloring agent includes, for example, a turmeric extract, riboflavin, carotin solution, and titanium oxide.

The surfactant includes, for example, polyoxyethylene hydrogenated castor oil, glycerin monostearate, sorbitan monostearate, sorbitan monolaurate, polyoxyethylene polyoxypropylene, polysolvates, sodium laurylsulfate, macrogols, and sucrose fatty acid ester.

The plasticizer includes, for example, triethyl citrate, polyethylene glycol, triacetin, and cetanol.

The pH regulating agent includes, for example, citric acid, malic acid, sodium hydrogen phosphate, and dipotassium hydrogen phosphate.

The refreshing agent includes, for example, 1-menthol and mentha water.

The suspending agent includes, for example, kaolin, sodium carmellose, xanthane gum, and tragacanth.

The defoaming agent includes, for example, dimethyl polysiloxane and silicone deforming agent.

The thickening agent includes, for example, xanthane gum, tragacanth, methyl cellulose, and dextrin.

The dissolving aid includes, for example, ethanol, sucrose fatty acid ester, and macrogol.

In case of soft drinks, a particularly desired taste or flavor can be obtained by adding other physiologically active substances, minerals, vitamins, hormones, nutrients, and/or flavorings, to the present composition, in addition to the above-mentioned additives.

BRIEF DESCRIPTION OF THE DRAWINGS

FIG. 1 shows durable swimming time of rats in forced swimming by administration of the present liquid preparation (plant worms and muirapuama), a single liquid preparation of plant worms, and muirapuama, respectively, and a control (purified water).

FIG. 2 shows total intakes of the present liquid preparation (plant worms and muirapuama), a single liquid preparation of plant worms and muirapuama, respectively, and a control (purified water) by exercise groups and non-exercise group.

DETAILED DESCRIPTION OF THE INVENTION

The present invention will be described in detail below, referring to Examples and Test Examples, and drawings.

EXAMPLE 1

| Formulation | |
|---|---|
| Plant worms | 100 mg (in terms of bulk natural drug) |
| Muirapuama | 300 mg (in terms of bulk natural drug) |
| Agkistrodon | 250 mg (in terms of bulk natural drug) |
| Taurine | 500 mg |
| Ginseng | 600 mg (in terms of bulk natural drug) |
| Astragalus | 300 mg (in terms of bulk natural drug) |
| Polygonati root | 300 mg (in terms of bulk natural drug) |
| Licorice root | 150 mg (in terms of bulk natural drug) |
| *Poria sclerotium* | 300 mg (in terms of bulk natural drug) |
| Rehmannia root | 200 mg (in terms of bulk natural drug) |
| Japanese angelica root | 200 mg (in terms of bulk natural drug) |
| Lycii fruit | 200 mg (in terms of bulk natural drug) |
| Cinnamon bark | 150 mg (in terms of bulk natural drug) |
| Velvet horn | 300 mg (in terms of bulk natural drug) |
| Barren-worts | 1000 mg (in terms of bulk natural drug) |
| Vitamin $B_2$ | 5 mg |
| Vitamin $B_6$ | 5 mg |
| Anhydrous caffeine | 50 mg |

The foregoing components were further mixed with appropriate amounts of sodium citrate, malic acid, sucrose, D-sorbitol solution, benzoic acid, polyoxyethylene hydrogenated castor oil and distilled water to make 50 ml of liquid preparation.

EXAMPLE 2

| Formulation | |
|---|---|
| Plant worms | 150 mg (in terms of bulk natural drug) |
| Muirapuama | 350 mg (in terms of bulk natural drug) |
| Agkistrodon | 300 mg (in terms of bulk natural drug) |
| Taurine | 500 mg |
| Ginseng | 600 mg (in terms of bulk natural drug) |
| Astragalus root | 300 mg (in terms of bulk natural drug) |
| Polygonati root | 300 mg (in terms of bulk natural drug) |
| Licorice | 150 mg (in terms of bulk natural drug) |
| *Poria sclerotium* | 300 mg (in terms of bulk natural drug) |

-continued

| Formulation | |
|---|---|
| Rehmannia root | 200 mg (in terms of bulk natural drug) |
| Japanese angelica root | 200 mg (in terms of bulk natural drug) |
| Lycii fruit | 200 mg (in terms of bulk natural drug) |
| Cinnamon bark | 150 mg (in terms of bulk natural drug) |
| Velvet horn | 300 mg (in terms of bulk natural drug) |
| Barren-worts | 1000 mg (in terms of bulk natural drug) |
| Vitamin $B_2$ | 5 mg |
| Vitamin $B_6$ | 5 mg |
| Anhydrous caffeine | 50 mg |

The foregoing components were further mixed with appropriate amounts of citric acid, sodium citrate, sucrose, D-sorbitol solution, benzoic acid, polyoxyethylene hydrogenated castor oil and distilled water to make 50 ml of liquid preparation.

EXAMPLE 3

| Formulation | |
|---|---|
| Plant worms | 300 mg (in terms of bulk natural drug) |
| Muirapuama | 300 mg (in terms of bulk natural drug) |
| Agkistrodon | 250 mg (in terms of bulk natural drug) |
| Taurine | 500 mg |
| Ginseng | 600 mg (in terms of bulk natural drug) |
| Astragalus root | 300 mg (in terms of bulk natural drug) |
| Licorice root | 100 mg (in terms of bulk natural drug) |
| *Poria sclerotium* | 250 mg (in terms of bulk natural drug) |
| Rehmannia root | 300 mg (in terms of bulk natural drug) |
| Japanese angelica root | 300 mg (in terms of bulk natural drug) |
| *Cistanchis caulis* | 300 mg (in terms of bulk natural drug) |
| Chinese gutta percha | 300 mg (in terms of bulk natural drug) |
| Schisandra fruit | 200 mg (in terms of bulk natural drug) |
| Cinnamon bark | 200 mg (in terms of bulk natural drug) |
| Velvet horn | 300 mg (in terms of bulk natural drug) |
| Barren-worts | 1000 mg (in terms of bulk natural drug) |
| Vitamin $B_2$ | 5 mg |
| Vitamin $B_6$ | 5 mg |
| Anhydrous caffeine | 50 mg |

The foregoing components were further mixed with appropriate amounts of citric acid, sodium citrate, sucrose, D-sorbitol solution, benzoic acid, polyoxyethylene hydrogenated oil and distilled water to make 50 ml of liquid preparation.

EXAMPLE 4

| Formulation | |
|---|---|
| Plant worms | 330 mg (in terms of bulk natural drug) |
| Muirapuama | 450 mg (in terms of bulk natural drug) |
| Agkistrodon | 400 mg (in terms of bulk natural drug) |
| Taurine | 500 mg |
| Ginseng | 600 mg (in terms of bulk natural drug) |
| Astragalus root | 300 mg (in terms of bulk natural drug) |
| Licorice root | 100 mg (in terms of bulk natural drug) |
| *Poria sclerotium* | 250 mg (in terms of bulk natural drug) |
| Rehmannia root | 300 mg (in terms of bulk natural drug) |
| Japanese angelica root | 300 mg (in terms of bulk natural drug) |
| *Cistanchis caulis* | 300 mg (in terms of bulk natural drug) |
| Chinese gutta percha | 300 mg (in terms of bulk natural drug) |
| Schisandra fruit | 200 mg (in terms of bulk natural drug) |
| Cinnamon bark | 200 mg (in terms of bulk natural drug) |
| Velvet horn | 300 mg (in terms of bulk natural drug) |
| Barren-worts | 1000 mg (in terms of bulk natural drug) |
| Vitamin $B_2$ | 5 mg |
| Vitamin $B_6$ | 5 mg |
| Anydrous caffeine | 50 mg |

The foregoing components were further mixed with appropriate amounts of sodium citrate, malic acid, sucrose, D-sorbitol solution, benzoic acid, polyoxyethylene hydrogenated oil and distilled water to make 50 ml of liquid preparation.

EXAMPLE 5

| Formulation | |
|---|---|
| Plant worms | 100 mg (in terms of bulk natural drug) |
| Muirapuama | 300 mg (in terms of bulk natural drug) |
| Rehmannia root | 1500 mg (in terms of bulk natural drug) |
| Barren-worts | 500 mg (in terms of bulk natural drug) |
| Eleuterococc | 750 mg (in terms of bulk natural drug) |
| Polygonati root | 750 mg (in terms of bulk natural drug) |
| Velvet horn | 250 mg (in terms of bulk natural drug) |
| Ginseng | 3000 mg (in terms of bulk natural drug) |
| Ophiopogon tuber | 1200 mg (in terms of bulk natural drug) |
| Schisandra fruit | 500 mg (in terms of bulk natural drug) |
| Polygoni multiflori root | 750 mg (in terms of bulk natural drug) |
| Cinnamon bark | 500 mg (in terms of bulk natural drug) |

The foregoing components were uniformly mixed with appropriate amounts of mannitol, hydroxypropyl cellulose, magnesium metasilicate aluminate, aspartame and flavoring and made into three packages of granules.

EXAMPLE 6

| Formulation | |
|---|---|
| Plant worms | 300 mg (in terms of bulk natural drug) |
| Muirapuama | 300 mg (in terms of bulk natural drug) |
| Rehmannia root | 1000 mg (in terms of bulk natural drug) |
| Polygonati root | 500 mg (in terms of bulk natural drug) |
| Velvet horn | 250 mg (in tenns of bulk natural drug) |
| Ginseng | 2000 mg (in terms of bulk natural drug) |
| Vitamin B$_2$ | 10 mg |
| Vitamin B$_6$ | 5 mg |

The foregoing components were uniformly mixed with appropriate amounts of magnesium mctasilicate aluminate, polysolvate 60 and propylene glycol, and the resulting mixture was uniformly filled into soft capsules to obtain 9 capsules of preparate.

EXAMPLE 7

| Formulation | |
|---|---|
| Plant worms | 100 mg (in terms of bulk natural drug) |
| Muirapuama | 200 mg (in terms of bulk natural drug) |
| Barren-worts | 500 mg (in terms of bulk natural drug) |
| Velvet horn | 200 mg (in terms of bulk natural drug) |
| Ginseng | 600 mg (in terms of bulk natural drug) |
| Polygonium multiflori root | 300 mg (in terms of bulk natural drug) |
| Bovine bile | 650 mg (in terms of bulk natural drug) |
| L-arginine hydrochloride | 100 mg |
| dl-carnitine chloride | 50 mg |
| Vitamin A | 2000 I.U. |
| Vitamin B$_1$ | 20 mg |
| Vitamin B$_2$ | 15 mg |
| Vitamin B$_6$ | 5 mg |
| Vitamin B$_{12}$ | 10 µg |
| Nicotinic acid amide | 20 mg |
| Calcium pantothenate | 30 mg |
| Vitamin C | 50 mg |
| Vitamin E | 5 mg |

The foregoing components were uniformly mixed with appropriate amounts of sodium hydrogen carbonate, polyvinyl pyrrolidone, light anhydrous silicic acid, magnesium stearate, polyethylene glycol, polysolvate 80 and flavoring to obtain 9 tablets of preparate.

TEST EXAMPLE 1

The following groups, each consisting of 7 male SD rats having an average body weight of 200 g, were tested by orally administering predetermined equal volumes of the following liquid preparations and subjecting the rats to forced swimming to determine durable swimming time.

Group A: administered with the present liquid preparation (plant worms : 0.2 w/v %+muirapuama: 0.6 w/v % in terms of bulk natural drugs)

Group B: administered with a single liquid preparation of plant worms (0.8 w/v % in terms of bulk natural drug)

Group C: administered with a single liquid preparation of muirapuama (0.8 w/v % in terms of bulk natural drug)

Group D: control (only purified water)

Results of durable swimming time of groups A, B, C and D are shown in FIG. 1.

As is evident from FIG. 1, the durable swimming time is much more extended in the case of Group A with the present liquid preparation than those in the cases of Groups B and C with the single liquid preparations.

TEST EXAMPLE 2

Male SD rats having an average body weight of 200 g were divided into the following exercise groups each consisting of 5 rats and non-exercise groups each consisting of 7 rats, and the exercise groups were subjected to forced swimming tests by conducting forced swimming for 30 minutes per day for a total 10 days while applying about 10% weight load per body weight to the respective rats, and by carrying out a two-bottle selective test with the following liquid preparations from the first day until the 10th day from the application of forced swimming load to determine their total intakes. The non-exercise groups were also tested in the same manner as above without any application of forced swimming under the weight load.

Group A: intake of the present liquid preparation (plant worms: 0.2 w/v %+muirapuama: 0.6 w/v % in terms of bulk natural drugs)

Group B: intake of a single liquid preparation of plant worms (0.8 w/v % in terms of original natural drug)

Group C: intake of a single liquid preparation of muirapuama (0.8 w/v % in terms of bulk natural drug)

Group D: control (intake of purified water)

The total intakes of the exercise groups and the non-exercise groups were compared, and the results are shown in FIG. 2.

As is evident from FIG. 2, the total intake of the present liquid preparation A by the exercise group is drastically increased, as compared with the total intakes of the single liquid preparations B and C by the exercise groups.

What is claimed is:

1. A composition comprising about 0.5 to 8 parts by weight muirapuama in an organic solvent extract from a muirapuama-containing root of shrubs of the family Olacaceae and about 1 part by weight of plant worm active ingredient in an organic solvent extract from at least one plant worm of the family Clavicipitaceae.

* * * * *